US010858311B2

(12) United States Patent
Taube et al.

(10) Patent No.: US 10,858,311 B2
(45) Date of Patent: Dec. 8, 2020

(54) METHOD FOR PRODUCING ISOCYANATES

(71) Applicant: Covestro Deutschland AG, Leverkusen (DE)

(72) Inventors: Wolfgang Taube, Neuss (DE); Rainer Bruns, Bergisch Gladbach (DE); Artur Mausbach, Dormagen (DE)

(73) Assignee: Covestro Deutschland AG, Leverkusen (DE)

( * ) Notice: Subject to any disclaimer, the term of this patent is extended or adjusted under 35 U.S.C. 154(b) by 0 days.

(21) Appl. No.: 16/619,540

(22) PCT Filed: Jun. 6, 2018

(86) PCT No.: PCT/EP2018/064851
§ 371 (c)(1),
(2) Date: Dec. 5, 2019

(87) PCT Pub. No.: WO2018/224530
PCT Pub. Date: Dec. 13, 2018

(65) Prior Publication Data
US 2020/0131120 A1    Apr. 30, 2020

(30) Foreign Application Priority Data
Jun. 8, 2017 (EP) .................... 17175068

(51) Int. Cl.
C07C 263/10 (2006.01)
C07C 263/20 (2006.01)

(52) U.S. Cl.
CPC .......... *C07C 263/10* (2013.01); *C07C 263/20* (2013.01)

(58) Field of Classification Search
None
See application file for complete search history.

(56) References Cited

U.S. PATENT DOCUMENTS 4,847,408 A   7/1989  Frosch et al.
5,633,396 A   5/1997  Bischof et al.
              (Continued)

FOREIGN PATENT DOCUMENTS

EP     2463273 A1    6/2012
WO  2013/029918 A1    3/2013

OTHER PUBLICATIONS

International Search Report, PCT/EP2018/064851, dated Jul. 26, 2018, Authorized officer: Wolfgang Fitz.

*Primary Examiner* — Amy C Bonaparte
(74) *Attorney, Agent, or Firm* — Donald R. Palladino (57) ABSTRACT

The invention relates to a method for preparing an isocyanate by phosgenating the corresponding primary amine in the gas phase, wherein the gaseous reaction product mixture is cooled by being brought into contact with at least one flow stream of a quenching liquid in a quenching zone, wherein the quenching liquid used in total comprises, based on the total mass, organic solvents in a proportion of maximally 50.0% by mass, and the remainder of up to 100% by mass consists of at least the isocyanate to be produced, thereby obtaining a mixture of the reaction product mixture and the quenching liquid. Furthermore, the mixture obtained in this manner of the reaction product mixture and the quenching liquid is separated into a liquid and a gaseous phase in a collection zone, and a liquid solvent intermediate flow comprising more than 50.0% by mass of organic solvents, based on the total mass of the liquid solvent intermediate flow, is conducted into the collecting zone and/or into a collecting tank arranged fluidically downstream of the collection zone for the liquid phase obtained in the collection zone.

22 Claims, 4 Drawing Sheets

(56) References Cited

U.S. PATENT DOCUMENTS

| | | |
|---|---|---|
| 6,803,482 B2 | 10/2004 | Jenne et al. |
| 6,838,578 B2 | 1/2005 | Leimkuhler et al. |
| 6,930,199 B2 | 8/2005 | Meyn et al. |
| 6,974,880 B2 | 12/2005 | Biskup et al. |
| 7,754,915 B2 | 7/2010 | Herold et al. |
| 2003/0069441 A1 | 4/2003 | Leimkuhler et al. |
| 2003/0230476 A1 | 12/2003 | Brady et al. |
| 2004/0068137 A1 | 4/2004 | Herold et al. |
| 2005/0070734 A1 | 3/2005 | Wolfert et al. |
| 2007/0043233 A1 | 2/2007 | Sanders et al. |
| 2008/0027242 A1 | 1/2008 | Knosche et al. |
| 2008/0146834 A1 | 6/2008 | Pohl et al. |
| 2008/0167490 A1 | 7/2008 | Pohl et al. |
| 2008/0200722 A1 | 8/2008 | Wolfert et al. |
| 2010/0152484 A1 | 6/2010 | Biskup et al. |
| 2010/0160673 A1 | 6/2010 | Bruns et al. |
| 2011/0257428 A1 | 10/2011 | Knoesche et al. |
| 2012/0004445 A1 | 1/2012 | Lehr et al. |
| 2012/0123152 A1 | 5/2012 | Bruns et al. |
| 2015/0368190 A1 | 12/2015 | Steffens et al. |
| 2016/0152558 A1 | 6/2016 | Steffens et al. |

METHOD FOR PRODUCING ISOCYANATES

CROSS-REFERENCE TO RELATED APPLICATION

This application is a U.S. National Phase application under 35 U.S.C. §371 of International Application No. PCT/EP2018/064851, filed Jun. 6, 2018, which claims priority to European Patent Application EP17175068.0, filed Jun. 8, 2017, which are each incorporated herein by reference.

FIELD

The invention relates to a process for preparing an isocyanate by phosgenating the corresponding primary amine in the gas phase, in which the gaseous reaction product mixture is cooled down by contacting with at least one stream of a quench liquid in a quench zone, where the total quench liquid used, based on its total mass, comprises organic solvents in a proportion of at most 50.0% by mass, where the remainder to 100% by mass consists of at least the isocyanate to be prepared, to obtain a mixture of reaction product mixture and quench liquid; wherein the mixture of reaction product mixture and quench liquid thus obtained is also separated in a collecting zone into a liquid phase and a gaseous phase, with introduction of a liquid solvent stream comprising more than 50.0% by mass of organic solvents, based on the total mass of the liquid solvent stream, into the collecting zone and/or into a collecting tank for the liquid phase obtained in the collecting zone which is disposed in flow direction downstream of the collecting zone.

BACKGROUND

There have long been descriptions in the prior art of the preparation of isocyanates, especially diisocyanates, in the gas phase, which is utilized industrially, particularly for preparation of tolylene diisocyanate, xylylene diisocyanate, pentane 1,5-diisocyanate, hexamethylene 1,6-diisocyanate, isophorone diisocyanate and diisocyanatodicyclohexylmethane. In all processes, a gaseous crude product is obtained that comprises at least isocyanate, hydrogen chloride and any unconverted phosgene (phosgene is generally used in excess), and which has to be subjected to further workup in order to obtain the desired isocyanate in pure form.

Such a process is described, for example, in EP 0 289 840 B1. The diisocyanates formed in a tubular reactor are thermally unstable at the reaction temperatures of up to 500° C. Rapid cooling of the reaction gases after the phosgenation reaction to temperatures below 150° C. is therefore necessary to avoid the formation of unwanted by-products by the thermal breakdown of diisocyanate or by a further reaction. In EP 0 289 840 B1 or EP 0749 958 B1, for this purpose, the gaseous mixture that leaves the reaction space continuously and includes diisocyanate, phosgene and hydrogen chloride is introduced into an inert solvent, e.g. dichlorobenzene.

There are also known processes that use heat exchangers to cool down the reaction gases and/or expand the gases under reduced pressure (DE 101 58 160 A1).

It is preferable in the current prior art to bring about the cooling of the reaction gases by injecting liquids that are inert under the reaction conditions with very substantial condensation of the isocyanate formed. This is done in what is called a cooling or quenching zone. The aim is, during the cooling, to largely prevent further reaction in the liquid phase to give unwanted by-products (for example isocyanurates, biurets, allophanates, carbodiimides or ureas).

In the process according to WO 2005/123665 A1, attempts are made to reduce the dwell time between the end of the reaction and cooling zone by the presence of a region with reduced flow cross section between the reaction zone and the zone in which the termination of reaction is brought about. Suitable liquids to be injected include solvent, isocyanate or mixtures of solvent and isocyanate.

WO 2011/003532 A1 also discloses a process for rapid cooling of the gaseous reaction mixture by injecting a quench liquid into the gas mixture flowing continuously from the reaction zone into the downstream quench zone. Suitable quench liquids mentioned are solvent, isocyanate or solvent/isocyanate mixtures.

The injection of quench liquid by means of at least two spray nozzles disposed at the entrance to the quench zone is disclosed in EP 1 403 248 A1. Suitable quench liquids here are organic solvents or a mixture of different organic solvents that do not react with the diisocyanate formed. A solution of the diisocyanate formed in a suitable organic solvent can also be used, which reduces the amount of solvent used. In this case, the proportion by volume of the solvent in the quench liquid is from 40% to 90%, i.e. the proportion by volume of isocyanate is up to 60%. The diameter of the quench zone may be greater or smaller than the diameter of the reaction zone.

This system is optimized according to the teaching of EP 1 935 875 A1 in that, to stop the reaction, the reaction mixture is conducted out of the reaction space through a cooling section into which liquids are injected into two zones, such that the direct cooling in the cooling section is effected in one stage (i.e. in the terminology of this application: obtaining just a single condensation mixture) in two or more cooling zones connected in series. The diisocyanate produced is thus obtained in a common condensation mixture. This mixture is preferably collected in a liquid collecting vessel arranged below the cooling section. This condensation mixture can be discharged to separate off the isocyanate prepared or, preferably after cooling, partly recycled to one or more cooling zones of the cooling section. The stream recycled in this way, corresponding to the cooling liquid in the second cooling zone, especially contains 30% to 90% by weight of solvent and 10% to 90% by weight of isocyanate. The addition of a solvent stream to the liquid collecting tank or to a collecting tank downstream thereof for the condensation mixture is not disclosed in this document.

As well as the condensation mixture in the collecting vessel, a gas stream comprising at least hydrogen chloride, phosgene, optionally solvent, and the isocyanate prepared is obtained downstream of the cooling section. This gas stream is removed from the collecting vessel and sent to a wash column, where it is largely freed of its isocyanate components. This wash is preferably effected in countercurrent with solvent. The wash phase thus obtained, consisting of diisocyanate and predominantly of solvent (80% to 99.99% by weight), in a preferred embodiment, is used as quench liquid for the first cooling zone of the cooling section. In the downstream cooling zone(s), as already outlined above, preference is given to using the condensation mixture from the collecting vessel (containing 10% to 70% by weight of isocyanate and 30% to 90% by weight of solvent) as quench liquid. It is realistically to be expected in this procedure (solvent content of the cooling liquid used in the first cooling zone not below 80% by weight and solvent content of the cooling liquid used in the second cooling zone and any further cooling zones not below 30% by weight in each case) is that the solvent content in the cooling liquid used overall will regularly be more than 50% by weight.

EP 1 935 876 A1 likewise mentions the use of various suitable quench liquid streams. Reference is also made to the use of the scrubbing liquid from the gas scrubbing of the vapor leaving the condensate collecting vessel downstream of the quench as quench liquid. Also mentioned is the possibility of using isocyanate as quench liquid (paragraph [0032]).

Multiple cooling zones in the quench stage are also referenced by EP 2 196 455 A1. This is the first reference to the integration of the cooling zones of multiple reactors with a quench stage. Here too, the option of using isocyanate as quench liquid is mentioned (paragraph [0055]).

Application WO 2007/014936 A2, Method for producing isocyanates (in the gas phase), describes a quench zone in which the gaseous crude product is cooled down rapidly by injecting a quench liquid. In this quench zone, the reaction mixture consisting essentially of the isocyanates, phosgene and hydrogen chloride is mixed vigorously with the liquid injected. The mixing is effected in such a way that the temperature of the reaction mixture is lowered proceeding from 200 to 570° C. down to 100 to 200° C., and the isocyanate present in the reaction mixture is transferred wholly or partly to the injected liquid droplets as a result of condensation, while the phosgene and the hydrogen chloride remain essentially completely in the gas phase. Possible quench liquids mentioned are solvent, isocyanate and solvent/isocyanate mixtures. The injection of a quench liquid is mentioned for cooling of the reaction mixture and selective dissolution of the diisocyanate formed in the solvent, with a first separation into a liquid phase and a gas phase comprising predominantly phosgene and hydrogen chloride as constituents. The two phases are then sent to an appropriate workup. There is no discussion of optimization options for this process step.

WO 2010/063665 A1 refers to a possible problem with the quench variants mentioned so far. If at least some of the quench liquid is withdrawn from the collecting vessel downstream of the quench, i.e. the liquid crude product mixture, it is possible that solids that can block the quench nozzles may be present. Various techniques, for example centrifuging, distilling off the liquid component intended for the quench or filtering, are described. In order to adjust the temperature of the selected quench stream for the stated problem, the stream can be cooled or heated up by means of a heat exchanger. This document discloses (page 12 lines 6 to 9, page 13 second paragraph) various sources for the quench medium: a substream 15 branched off from the phase separator 9 downstream of the quench 3 (which necessarily also contains isocyanate liquefied in the quench), fresh solvent 19, a portion of the liquid phase 13 obtained in the phase separator, and a substream of the biphasic product stream 7.

WO 2010/115908 A2 discloses a specific embodiment of the quench. In order to prevent further reactions of the reaction gas in or downstream of the quench stage, the quench nozzles and their arrangement are designed such that largely complete wetting of the wall is effected in the quench region. This affects the entire reaction mixture. Quench liquids proposed are solvents and mixtures with isocyanate or crude mixture from the phosgenation reaction, optionally after removal of particles. The proportion of isocyanate in the liquid with which the walls are wetted or in the quench medium may be in the range from 0 to 100 percent (page 11 lines 5 to 8).

EP 2 463 273 A1 discloses a process variant for isocyanate concentrations of greater than 70% by mass in the liquid bottom product leaving the quench zone. The stream leaving the quench zone in gaseous form is guided directly into a jacket-cooled condenser without passing through a wash column. The remaining gas stream is sent directly to the phosgene recovery. In spite of the high temperature and high isocyanate concentration in the liquid bottom product from the quench zone, no statements are made as to residual isocyanate contents in the remaining gas stream. The condensate stream is combined with the condensate of the vapor stream, which results from expansion of the liquid bottom product from the quench zone, and recycled as quench liquid.

WO 2013/029918 A1 concerns a process for preparing isocyanates by reacting the corresponding amines present in at least one reactant stream A with phosgene present in at least one reactant stream P in a reactor system comprising at least one mixing zone and at least one reaction zone, wherein reactant stream A and/or reactant stream P optionally contain one or more inert substances, and wherein, in periods in which the flow rate $S^x$ of the amines used is below the flow rate $S^0$ of the amines used in operation at the rated capacity of the reactor plant by comparison with operation at the rated capacity of the reactor, (i) the ratio of phosgene to amine is increased and/or (ii) the concentration of the inert substance(s) in the amine-containing reactant stream A and/or the phosgene-containing reactant stream P is increased.

This patent application also describes, inter alia, the performance of the phosgenation in the gas phase. In order to reduce or to avoid the formation of unwanted by-products and additionally also to prevent breakdown of the isocyanate formed, the reaction gas is preferably cooled immediately after the reaction in a quench zone. For this purpose, a preferably liquid quench medium is added. By evaporation of the quench medium, it absorbs heat, which leads to rapid cooling of the reaction gas.

The quench medium used for cooling preferably contains a solvent. In this case, it is preferable to add the solvent to the quench medium before addition thereof to the quench stage in order to compensate for solvent losses in the quench medium. The addition of a solvent stream to a collecting zone downstream of the quench zone, in which the evaporated quench medium is separated from the remaining liquid phase containing the isocyanate, is not disclosed in this application.

In another embodiment according to WO 2013/029918 A1, it is likewise possible for the quench medium to contain or consist of a portion of the product stream cooled in the quench zone.

WO 2014/122180 A1 concerns a process regime which makes it possible to completely dispense with recycling of the condensation mixture obtained in the quench zone into the quench. For this purpose, the gas phase obtained in the quench is partially condensed before being introduced into a scrubbing column, and the resulting condensate is used as additional quench liquid instead of recycled condensation product.

WO 2015/011070 A1 concerns the prevention of deposits in the region of the quench. What is taught is to keep the temperature of the wall of the reaction zone immediately above the quench zone at a value of at most 15% below the maximum temperature of the wall of the reaction zone reported in kelvin. Suitable quench liquids mentioned are solvent, isocyanate and mixtures of solvent and isocyanate.

Figure 1:
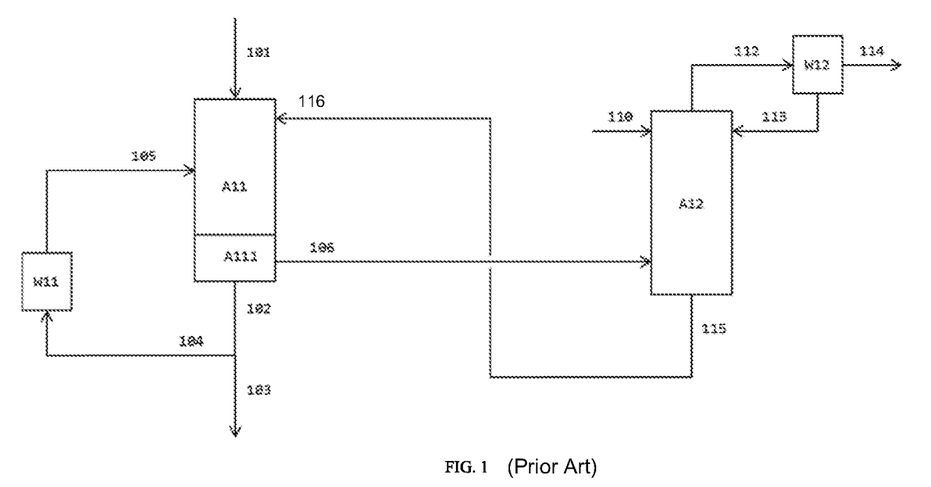
FIG. 1 illustrates a process flow of a two-stage quench of a crude product gas stream.

In summary, it can be stated that, in the prior art, the injection of liquids that are inert under the reaction conditions into the crude product gas stream is the preferred variant for rapid cooling and condensation of the product. The at least two-stage quench in which a predominantly solvent-containing quench liquid is used in a first quench stage—viewed in flow direction of the product gas mixture, and a quench liquid consisting to a considerable degree of the isocyanate to be formed is used in a downstream second quench has been found here to be particularly advantageous. One possible embodiment of this method is elucidated hereinafter with reference to the first figure (FIG. 1):

The gaseous crude product (101), consisting primarily of isocyanate, hydrogen chloride and phosgene used in a superstoichiometric amount, is rapidly cooled in the quench (A11) by injecting quench liquid (105 and 116) in order to avoid unwanted further reactions. The liquid stream (102) that leaves the collecting container (A111) in the lower region of the quench and contains mainly isocyanate and quench liquid (especially 10% to 70% by weight of isocyanate and 30% to 90% by weight of solvent; cf. EP 1 935 875 A1, paragraph [0042]), is guided partly to the product purification (103) and partly recycled to the quench (104) via the quench cooler (W11) as quench liquid.

The material flow (106) that leaves the quench in gaseous form, comprising mainly evaporated quench liquid, hydrogen chloride and phosgene, is sent to a wash column (A12) to remove residual contents of isocyanate as far as possible from the vapor stream. The greater the content of isocyanates in the material flow (106) fed in, the higher the flow rate of wash liquid stream (solvent) supplied at the top of the wash column has to be, and the more separation plates are required for reliable retention. The vapors (112) from the scrubbing column pass through a condenser (vapor condenser W12). The wash liquid stream is composed of the condensate (113) from the condenser (W12) and additional solvent (110). The virtually isocyanate-free vapor stream (114) contains mainly phosgene and hydrogen chloride. The liquid bottoms effluent (115) contains mainly solvent and is appropriately fed as quench liquid to the quench.

Operational experience has shown that the operation of the quench in this way, although possible in principle and superior to many other process regimes, is not without disadvantages. In particular, contrary to any expectation, it has been observed that, particularly in the region of the first quench in flow direction of the product gas mixture, operated predominantly with solvent, deposits are formed over time, and these in the worst case can necessitate shutdown and cleaning of the reactor. Moreover, solids formed in or introduced into the reaction zone or quench zone and high boilers get into the quench cooler (W11) and the quench nozzles with the liquid quench product and can cause soiling therein. In addition, in the case of injection of a stream having a high solvent content (solvent content more than 50%) into the quench zone, the evaporation of a portion of the solvent generates a large vapor stream which contributes considerably to the total volume of the gas stream leaving the quench stage and in this way increases the expenditure associated with the removal of isocyanate entrained in this gas stream, for instance in that this results in greater dimensions of the apparatuses used. Moreover, there is the risk that the large amount of vapor will entrain any solid deposits present out of the reactor into the downstream separation of isocyanate from the gaseous stream obtained in the quench and will lead to blockages in apparatuses therein.

SUMMARY

Building on this prior art, there was therefore a need for further optimization of the quench of a gaseous crude isocyanate product. More particularly, it was desirable to improve the quench to the effect that deposits in the quench region are avoided or at least reduced, without significantly impairing the quality and processibility of the resultant condensation product. It was also desirable to minimize the content of solvent in the condensation product obtained in the quench because it is necessary to separate off the solvent present therein again in the workup.

Taking account of the above, the present invention provides a process for preparing an isocyanate by phosgenating the corresponding primary amine in the gas phase, comprising the steps of:

(i) providing a gaseous stream of a primary amine;
(ii) providing a gaseous phosgene stream;
(iii) mixing the gaseous stream of the primary amine from step (i) and the gaseous phosgene stream from step (ii) to give a gaseous reaction mixture while maintaining a stoichiometric excess of phosgene relative to primary amino groups in a mixing zone and conducting the gaseous reaction mixture thus obtained through a reaction zone for reaction of the primary amine with phosgene to obtain a gaseous reaction product mixture;
(iv) cooling the gaseous reaction product mixture obtained after passage through the reaction zone from step (iii) by contacting with at least one stream of a quench liquid in a quench zone, where the total quench liquid used, based on its total mass, comprises organic solvents in a proportion of at most 50.0% by mass, preferably at most 20.0% by mass, more preferably at most 10.0% by mass, most preferably 1.0% by mass, where the remainder to 100% by mass consists of at least the isocyanate to be prepared, to obtain a mixture of reaction product mixture and quench liquid;
(v) conducting the mixture of reaction product mixture and quench liquid obtained in step (iv) into a collecting zone for separation of liquid phase and gaseous phase to obtain a liquid phase comprising isocyanate and optionally solvent and a gaseous phase comprising hydrogen chloride, unconverted phosgene, unliquefied isocyanate and any evaporated solvent, with introduction of a liquid solvent stream comprising more than 50.0% by mass, especially at least 51.0% by mass, preferably at least 80.0% by mass, more preferably at least 90.0% by mass, most preferably at least 99.0% by mass, of organic solvents, based on the total mass of the liquid solvent stream, into the collecting zone and/or into a collecting tank for the liquid phase obtained in the collecting zone which is disposed in flow direction downstream of the collecting zone.

DETAILED DESCRIPTION

Completely surprisingly, it has been found that—by comparison with the prior art exemplified in FIG. 1—dispensing with the upper, predominantly solvent-containing quench stage in conjunction with introduction of a solvent stream into the collecting zone below the quench zone or into a collecting tank for the liquid phase obtained in the collecting zone which is in flow direction downstream has the effect that there are fewer deposits in the quench zone without affecting the quality of the product and without any deterioration in the processibility of the liquid crude product obtained in the collecting zone or in the collecting tank (for instance as a result of unwanted significant rise in viscosity), and also has the effect that the total amount of solvent used can be reduced.

According to the invention, the "total amount of quench liquid used in step (iv), based on its total mass," has a proportion of organic solvents of "at most 50.0% by mass, preferably at most 20.0% by mass, more preferably at most 10.0% by mass, most preferably 1.0% by mass". If exactly one stream of quench liquid is used in step (iv), this stream must meet these requirements on maximum solvent content. If two or more streams of quench liquid from different sources with different composition are used in step (iv), the solvent content value averaged over all the streams of quench liquid used in step (iv) (i.e. the proportion based on the total mass of the quench liquid used overall) must meet these requirements (preferably, each individual stream of quench liquid used in step (iv) meets the aforementioned requirements on maximum solvent content and otherwise consists of at least the isocyanate to be prepared). "Organic solvents" (solvents for the purposes of the invention are always organic solvents) here are organic diluents which have no phosgene-reactive groups and in which the isocyanate to be prepared is soluble under standard conditions (20° C., 1013 mbar) and which are liquid under standard conditions (20° C., 1013 mbar) and are added to the process, but of course differ from these. The amount of such solvents added to the process is known; the solvent content in the total amount of quench liquid used in step (iv) can be readily ascertained by the person skilled in the art from this and from the boundary conditions that are likewise known (site of addition, temperatures and pressures, flow rates of the other feedstocks). The proportion of the total amount of quench liquid used that does not originate from such solvents consists at least of isocyanate to be prepared.

In particular variants of the invention, a "collecting tank for liquid phase obtained in the collecting zone" is arranged "in flow direction" downstream of the collecting zone, meaning that the liquid phase from the collecting zone—if it is not recycled as quench liquid into step (iv), as envisaged in some embodiments elucidated in detail further down—flows into this collecting tank. If a production plant has multiple parallel-connected reaction lines controllable independently of one another (also referred to as reaction trains), it is advantageously possible to collect the liquid crude product from all the reaction lines in such a collecting tank and then send it to a common workup (especially distillation).

The "liquid phase comprising isocyanate and optionally solvent" obtained in step (v) is the liquid phase obtained in the collecting zone in the phase separation. In a first variant of the invention (namely in the case of introduction of liquid solvent stream solely into the collecting zone), this liquid phase always contains solvent, namely at least the solvent from the liquid solvent stream added in this way. In a second variant of the invention (namely in the case of introduction of the liquid solvent stream solely into the collecting tank), this liquid phase does not necessarily contain solvent since the solvent content in the quench liquid from step (iv) may also be zero. In a third variant of the invention, a liquid solvent stream is guided into the collecting zone and into the collecting tank; in this variant, the liquid phase obtained in the collecting zone also contains solvent. The "gaseous phase comprising hydrogen chloride, unconverted phosgene, unliquefied isocyanate and any evaporated solvent" obtained in step (v) is the gaseous phase obtained in the phase separation in the collecting zone.

There firstly follows a brief summary of various possible embodiments of the invention:

In a first embodiment of the invention, which can be combined with all other embodiments, step (iii) is conducted adiabatically, wherein composition and temperature of the gaseous stream of the primary amine in step (i) and of the phosgene stream in step (ii) are each chosen such that, in step (iii), a temperature in the range from 250° C. to 450° C., preferably in the range from 270° C. to 425° C., more preferably in the range from 280° C. to 420° C., is established in the mixing zone and in the reaction zone.

In a second embodiment of the invention, which can be combined with all other embodiments, the temperature of the quench liquid used in step (iv) is adjusted to a value in the range of 50° C. to 250° C., preferably 100° C. to 200° C., more preferably 120° C. to 190° C.

In a third embodiment of the invention, which can be combined with all other embodiments, the mass flow rate of the quench liquid used in step (iv) is chosen such that it is 2 times to 60 times, preferably 10 times to 50 times, more preferably 20 times to 40 times, the mass flow rate of gaseous stream of the primary amine from step (i).

In a fourth embodiment of the invention, which can be combined with all other embodiments, the temperature of the liquid solvent stream guided into the collecting zone or collecting tank in step (v) is adjusted to a value in the range of 120° C. to 200° C., preferably from 180° C. to 190° C.

In a fifth embodiment of the invention, which can be combined with all other embodiments except the sixth described below, the liquid solvent stream in step (v) is guided solely into the collecting zone (first variant of the invention), wherein the liquid solvent stream is guided into the collecting zone in such a mass flow rate that its proportion of the total mass of the liquid phase comprising isocyanate and solvent which is obtained in the collecting zone is in the range from 20% by mass to 80% by mass, preferably in the range of 40% by mass to 60% by mass.

In a sixth embodiment of the invention, which can be combined with all other embodiments except the fifth, the liquid solvent stream in step (v) is guided either (a) into the collecting tank (second variant of the invention) or (b) into the collecting tank and into the collecting zone (third variant of the invention), wherein the flow rate of the liquid solvent stream in each case is chosen so that the liquid solvent stream is present in an amount of 20% by mass to 80% by mass, preferably in the range of 40% by mass to 60% by mass, based on the total mass of the liquid phase comprising isocyanate and solvent which is obtained in the collecting tank.

In a seventh embodiment of the invention, which can be combined with all other embodiments, the contacting of the gaseous reaction product mixture with the quench liquid in step (iv) is effected by injecting the quench liquid into the gaseous reaction product mixture.

In an eighth embodiment of the invention, which is a particular configuration of the seventh embodiment, the contacting of the gaseous reaction product mixture with the quench liquid in step (iv) is effected in one stage.

In a ninth embodiment of the invention, which can be combined with all other embodiments, the gaseous phase comprising hydrogen chloride, unconverted phosgene, unliquefied isocyanate and any evaporated solvent which is obtained in step (v) is condensed, especially only partly condensed, in step (viii-1) by indirect cooling to obtain a liquid stream comprising isocyanate and optionally solvent and a gaseous stream comprising hydrogen chloride, phosgene, any unliquefied isocyanate and any unliquefied solvent.

In a tenth embodiment of the invention, which is a particular configuration of the ninth embodiment, the gaseous stream comprising hydrogen chloride, phosgene, any unliquefied isocyanate and any unliquefied solvent which is obtained in step (viii-1) is guided, in a step (viii-2), into a scrubbing column, where it is contacted with at least one liquid solvent stream as scrubbing liquid, giving a liquid stream comprising solvent and isocyanate and a gaseous stream comprising hydrogen chloride and phosgene.

In an eleventh embodiment of the invention, which can be combined with all other embodiments except for the ninth and tenth, the gaseous phase comprising hydrogen chloride, unconverted phosgene, unliquefied isocyanate and any evaporated solvent which is obtained in step (v) is guided, in a step (viii-2), into a scrubbing column (i.e. without prior condensation in step (viii-1)), where it is contacted with at least one liquid solvent stream as scrubbing liquid, giving a liquid stream comprising solvent and isocyanate and a gaseous stream comprising hydrogen chloride and phosgene.

In a twelfth embodiment of the invention, which is a particular configuration of the ninth and tenth embodiments, the gaseous phase comprising hydrogen chloride, unconverted phosgene and unliquefied isocyanate which is obtained in the collecting zone comprises evaporated solvent, wherein the liquid solvent stream guided into the collecting zone or collecting tank in step (v) comprises the liquid stream comprising isocyanate and solvent which is obtained in step (viii-1).

In a thirteenth embodiment of the invention, which is a particular embodiment of the tenth, eleventh and twelfth embodiments, step (viii-2) is performed in each case, wherein the liquid solvent stream guided into the collecting zone or collecting tank in step (v) comprises the liquid stream comprising solvent and isocyanate obtained in step (viii-2).

In a fourteenth embodiment of the invention, which is a particular embodiment of the twelfth and thirteenth embodiments, the solvent stream from step (v) does not comprises any further constituents apart from the liquid isocyanate mentioned and solvent-comprising streams from step (viii-1) and/or step (viii-2).

In a fifteenth embodiment of the invention, which can be combined with all other embodiments, advantageously especially with the twelfth, thirteenth or fourteenth embodiment, in step (v), the liquid solvent stream is guided at least temporarily into the collecting zone and into the collecting tank, wherein the conduits for this solvent stream that lead into the collecting zone and the collecting tank are controllable independently of one another (i.e. the mass flow rate through one of these conduits is regulatable independently of the other conduit).

In a sixteenth embodiment of the invention, which can be combined with all other embodiments, a portion of the liquid phase comprising isocyanate and optionally solvent which is obtained in the collecting zone in step (v) is cooled in a step (vi), preferably by indirect cooling, but is otherwise unchanged in its composition and is recycled into the quench zone from step (iv), especially with no use of any further streams of quench liquid.

In a seventeenth embodiment of the invention, which can be combined with all other embodiments, especially advantageously with the sixteenth embodiment, at least a portion of the liquid phase comprising isocyanate and optionally solvent which is obtained in the collecting zone in step (v), especially the portion not recycled into the quench zone from step (iv) in step (vi) in the sixteenth embodiment, is worked up in a step (vii) to give pure isocyanate.

In an eighteenth embodiment of the invention, which can be combined with all other embodiments, the liquid solvent stream guided into the collecting zone or collecting tank in step (v) contains exclusively solvents selected from the group consisting of aliphatic hydrocarbons [preferably decahydronaphthalene], aromatic hydrocarbons having no halogen substitution [preferably toluene or xylene, especially toluene], aromatic hydrocarbons having halogen substitution [preferably chlorobenzene, para-dichlorobenzene, ortho-dichlorobenzene, chlorotoluene or chloronaphthalene, especially ortho-dichlorobenzene] and mixtures of the aforementioned solvents, wherein
  the solvent optionally present in the quench liquid used in step (iv), if present, and
  the solvent contained in the liquid solvent stream used as scrubbing liquid in step (viii -2), if conducted, is the same in each case as the solvent contained in the liquid solvent stream guided into the collecting zone or collecting tank in step (v).

In a nineteenth embodiment of the invention, which can be combined with all other embodiments, the primary amine is selected from the group consisting of tolylenediamine, diphenylmethanediamine, xylylenediamine, pentane-1,5-diamine, hexamethylene-1,6-diamine, isophoronediamine, diaminodicyclohexylmethane and mixtures of the aforementioned compounds.

In a twentieth embodiment of the invention, which can be combined with all other embodiments, the same organic solvent is used in all steps of the process in which an organic solvent is used, and this organic solvent is selected from the group consisting of aliphatic hydrocarbons [preferably decahydronaphthalene], aromatic hydrocarbons having no halogen substitution [preferably toluene or xylene, especially toluene], aromatic hydrocarbons having halogen substitution [preferably chlorobenzene, para-dichlorobenzene, ortho-dichlorobenzene, chlorotoluene or chloronaphthalene, especially ortho-dichlorobenzene] and mixtures of the aforementioned organic solvents.

In a twenty-first embodiment of the invention, which is a particular embodiment of the twentieth embodiment, the organic solvent is ortho-dichlorobenzene.

The embodiments briefly outlined above and further possible configurations of the invention are elucidated in detail hereinafter. Various embodiments are combinable with one another as desired unless the opposite is clearly apparent to the person skilled in the art from the context.

In step (i), a stream of a primary amine in gaseous form is provided.

Suitable primary amines for the performance of this step are those which can be evaporated without decomposition, especially tolylenediamine (TDA hereinafter, especially meta-TDA), diphenylmethanediamine (often also called methylenediphenyldiamine, MDA hereinafter), xylylenediamine (XDA, especially meta-XDA), pentane-1,5-diamine (PDA hereinafter), hexamethylene-1,6-diamine (HDA hereinafter), isophoronediamine (IDPA hereinafter) and diaminodicyclohexylmethane (H12-MDA hereinafter). If the amines mentioned can be present in different isomeric forms without specification thereof, all isomer distributions are included. In principle, it is also possible to convert mixtures of the aforementioned amines, although this is generally not preferred.

Particular preference is given to TDA. Typically, TDA which is used with preference comprises 78.0% by mass to 82.0% by mass of 2,4-TDA and 18.0% by mass to 22.0% by mass of 2,6-TDA, based on the total mass of the 2,4- and 2,6-TDA isomers. Based on the total mass of the TDA, the 2,4- and 2,6-TDA isomers preferably account for a sum total of 95.0% by mass to 100% by mass, more preferably of 98.0% by mass to 100% by mass. Preferably, the content of TDA isomers having $NH_2$ groups in ortho positions to one another in the TDA used is less than 0.2% by mass, based on the total mass of the TDA used. Processes for providing TDA with the requirements mentioned are known to the person skilled in the art.

Methods of providing a gaseous amine stream for the performance of step (i) are known in principle to the person skilled in the art. Preferred embodiments are outlined hereinafter.

The amine can be converted to the gas phase in all evaporation apparatuses known from the prior art, especially in a falling-film evaporator. Preference is given to using those evaporation apparatuses in which a small volume of working contents is guided over a falling-film evaporator with a high circulation power.

In a preferred embodiment of the process of the invention, evaporation apparatuses in which a small volume of working contents is circulated through at least one micro heat exchanger or micro evaporator are used. The use of corresponding heat exchangers for the evaporation of amines is disclosed, for example, in EP 1 754 698 A2. Preference is given to using the apparatuses disclosed in paragraphs [0007] to [0008] and [0017] to [0039] of EP 1 754 698 A2 in the process of the invention.

For minimization of thermal stress on the amine, irrespective of the exact configuration of the evaporation apparatus, it is preferable to assist the evaporation operation by feeding in an inert gas such as $N_2$, He, Ar or the vapors of an inert solvent, preferably selected from the group consisting of aliphatic hydrocarbons [preferably decahydronaphthalene], aromatic hydrocarbons without halogen substitution [preferably toluene or xylene, especially toluene], aromatic hydrocarbons with halogen substitution [preferably chlorobenzene, para-dichlorobenzene, ortho-dichlorobenzene, chlorotoluene or chloronaphthalene, especially ortho-dichlorobenzene] and mixtures of the aforementioned organic solvents. If the amine is diluted in this way, preference is given to the use of an inert gas selected from the group consisting of $N_2$, He, Ar and mixtures thereof as diluent, dispensing with the use of vapors of an inert solvent.

In addition, the evaporation—and if required superheating—of the starting amine (especially to a temperature in the range from 200° C. to 430° C., preferably 250° C. to 420° C., more preferably 250° C. to 400° C.) is preferably effected in multiple stages in order to avoid unevaporated droplets in the gaseous amine stream. Especially preferred are multistage evaporation and superheating steps in which droplet separators are installed between the evaporation and superheating systems and/or the evaporation apparatuses also have the function of a droplet separator. Suitable droplet separators are known to those skilled in the art. After leaving the last superheater in flow direction, the gaseous amine preheated to its target temperature is sent to the mixing and reaction in step (iii) with an average dwell time of preferably 0.01 s to 60 s, even more preferably of 0.01 s to 30 s, especially preferably 0.01 s to 15 s. Irrespective of the configuration of the supply of the amine in detail, the risk of new droplet formation is preferably countered by means of technical measures, for example sufficient insulation for avoidance of radiative heat losses.

In step (ii), a gaseous phosgene stream is provided.

In the process of the invention, phosgene is used in excess relative to the amino groups to be converted. Preference is given to establishing a molar ratio of phosgene to amine groups of 1.1:1 to 20:1, more preferably 1.2:1 to 5.0:1. As described above for the amine, the phosgene is preferably also heated to a temperature in the range from 200° C. to 430° C., preferably 250° C. to 420° C., more preferably 250° C. to 400° C., and supplied to the mixing and reaction in step (iii) optionally diluted with an inert gas such as $N_2$, He, Ar or with the vapors of an inert solvent, preferably selected from the group consisting of aliphatic hydrocarbons [preferably decahydronaphthalene], aromatic hydrocarbons without halogen substitution [preferably toluene or xylene, especially toluene], aromatic hydrocarbons with halogen substitution [preferably chlorobenzene, para-dichlorobenzene, ortho-dichlorobenzene, chlorotoluene or chloronaphthalene, especially ortho-dichlorobenzene] and mixtures of the aforementioned organic solvents. If the phosgene is diluted, preference is given to the use of an inert gas selected from the group consisting of $N_2$, He, Ar and mixtures thereof as diluent, dispensing with the use of vapors of an inert solvent.

In step (iii), the amine and phosgene coreactants are mixed and reacted.

The separately heated amine and phosgene coreactants are preferably supplied via a nozzle arrangement to the mixing and conversion in step (iii). The nozzle arrangement for introduction of the amine and phosgene reactant gas streams may be configured in various ways known to the person skilled in the art; examples can be found, for example, in EP 2 199 277 B1, paragraphs [0017] to [0019], EP 1 449 826 B1, paragraphs [0011] to [0012], EP 1 362 847 B1, paragraphs [0011] to [0012], EP 1 526 129 B1, paragraphs [0009] to [0011] and EP 1 555 258 B1, paragraphs [0008] to [0011].

As well as the option already mentioned of diluting the gaseous stream of the primary amine and the gaseous phosgene stream, it is also possible to run a separate diluent gas stream (an inert gas such as $N_2$, He, Ar or the vapors of an inert solvent, preferably selected from the group consisting of aliphatic hydrocarbons [preferably decahydronaphthalene], aromatic hydrocarbons without halogen substitution [preferably toluene or xylene, especially toluene], aromatic hydrocarbons with halogen substitution [preferably chlorobenzene, para-dichlorobenzene, ortho-dichlorobenzene, chlorotoluene or chloronaphthalene, especially ortho-dichlorobenzene] and mixtures of the aforementioned organic solvents) directly into the mixing in step (iii). In this case, this diluent gas stream is preferably heated to a temperature in the range from 100° C. to 500° C., preferably 150° C. to 450° C., more preferably 150° C. to 400° C. If the mixing zone from step (iii) is supplied with such a diluent gas stream, preference is given to the use of an inert gas selected from the group consisting of $N_2$, He, Ar and mixtures thereof as diluent gas, dispensing with the use of vapors of an inert solvent.

The conversion in the reaction zone is preferably adiabatic. Adiabatic conversion means that controlled removal of the heat of reaction formed by a heat carrier medium is dispensed with. Therefore, the reaction enthalpy—apart from unavoidable heat losses—is reflected quantitatively in the temperature differential of product gas stream and reactant gas stream. More particularly, the invention also relates to a process in which step (iii) is conducted adiabatically and wherein composition and temperature of the gaseous stream of the primary amine in step (i) and the phosgene stream in step (ii) are each chosen such that, in step (iii), a temperature in the range from 250° C. to 450° C., preferably in the range from 270° C. to 425° C., more preferably in the range from 280° C. to 420° C., is established in the mixing zone and in the reaction zone. This means that the temperature at any point in the mixing zone and the reaction zone is within this range.

Mixing zone and reaction zone are disposed here preferably in a common technical apparatus for performance of chemical reactions, the reactor. In this arrangement, mixing zone and reaction zone generally have a fluid transition without the possibility of—as in the case of use of a separate mixing apparatus, which is also possible in principle—strict delimitation between the two. The reaction zone after mixing of the reactants serves to provide delay time in order to assure maximum conversion.

The reactor preferably has a round (especially circular symmetrical) cross section in the region of the mixing zone and in the region of the reaction zone. It is possible here for the entire reactor to be cylindrical. However, it is also possible that the cross section changes, as described, for example, in EP 1275639 B1, paragraph [0009], EP 1 275 640 A1, paragraph [0014], EP 1 403 248 B1, paragraphs [0014] to [0015], EP 193 5876 A1, paragraphs [0012] to [0016], and EP 2 196 455 B1, paragraphs [0015] to [0026] and [0027] to [0030]. Further details of the construction of suitable phosgenation reactors are known to those skilled in the art.

In the reaction zone, amine and phosgene are converted rapidly to the corresponding isocyanate, preferably adiabatically as described. The reaction is preferably conducted such that the amine is converted fully before entry into the quench zone described in detail further down.

In a preferred embodiment of the process of the invention, the throughput capacity of the reactor used under reaction conditions is >1.0 t of amine/h, preferably 2.0 to 50 t of amine/h, more preferably 5.0 to 15 t of amine/h. These values are more preferably applicable to tolylenediamine, 1,6-diaminohexane and isophoronediamine. "Throughput capacity" is understood to mean that the stated throughput capacity of amine per hour can be converted in the reactor.

Preferably, the reactant and product gases flow through the reactor without significant backmixing. This is ensured by a pressure gradient across the mixing zone and reaction zone, preferably across the mixing zone and reaction zone and the downstream quench zone. Preferably, the pressure gradient exists between the start of the mixing zone on the one hand and the exit from the quench zone on the other hand. Preferably, the absolute pressure at the start of the mixing zone is 200 mbar to 3000 mbar and that beyond the quench zone is 150 mbar to 2500 mbar. All that is essential here, however, is the maintenance of a pressure differential across the reaction zone, preferably across the reaction zone and the quench zone, preferably at least 40 mbar for assurance of the directed flow mentioned and good mixing of the reactants.

In step (iv), the isocyanate formed is rapidly cooled and largely liquefied ("quench").

What is meant by the requirement of the invention that "the total amount of quench liquid used, based on its total mass, has a proportion of organic solvents of at most 50.0% by mass, preferably at most 20.0% by mass, more preferably at most 10.0% by mass, most preferably 1.0% by mass, where the remainder to 100% by mass consists of at least the isocyanate to be prepared" is that, in the context of the present invention, the use of quench liquid with a high solvent content (more than 50.0% by mass, especially 51.0% by mass or more—such streams are regarded in the terminology of the present invention as "solvent streams") which is customary in the art is not employed. If the quench liquid used in step (iv) contains an organic solvent, it is preferably selected from the group consisting of aliphatic hydrocarbons [preferably decahydronaphthalene], aromatic hydrocarbons having no halogen substitution [preferably toluene or xylene, especially toluene], aromatic hydrocarbons having halogen substitution [preferably chlorobenzene, para-dichlorobenzene, ortho-dichlorobenzene, chlorotoluene or chloronaphthalene, especially ortho-dichlorobenzene] and mixtures of the aforementioned organic solvents.

After the phosgenation reaction in the reaction zone, the gaseous reaction product mixture comprising at least isocyanate to be prepared, hydrogen chloride and unconverted phosgene (since it is used superstoichiometrically) is guided into the quench zone, where the isocyanate formed is cooled down and hence (largely) condensed by contacting with, i.e. especially by injecting, quench liquid. Options for the construction and operation of a quench zone are known in principle from the prior art. If the demands of the invention with regard to the composition of the quench liquid are complied with, it is possible to use the apparatuses and methods from the prior art. Possible configurations of the quench zone are disclosed, for example, in EP 1 403 248 A1 and EP 1 935 875 A1. Compliance with the demands of the invention with regard to the composition of the quench liquid means that the total amount of quench liquid used in the overall quench step (iv) contains 0.0% by mass to 50.0% by mass of organic solvents, preferably 0.0% by mass to 20.0% by mass of organic solvents, more preferably 0.0% by mass to 10.0% by mass of organic solvents, based in each case on the total mass of the quench liquid used overall. If multiple streams of quench liquid are used, the aforementioned composition ranges are applicable at least to the proportion by mass of organic solvents averaged over all streams of quench liquid used, but preferably to each individual stream of quench liquid. In one embodiment elucidated in detail further down, a portion of the liquid phase obtained in the collecting zone in step (v), after cooling, is recycled into the quench from step (iv) (i.e. used as quench liquid). If this embodiment is used in the first or third variant of the invention (introduction of a liquid solvent stream in step (v) into the collecting zone), the quench liquid used in step (iv) will inevitably contain solvent. The proportion of solvents in the substream of liquid phase obtained in step (v) which is recycled in this way is preferably 2.0% by mass to 10.0% by mass, more preferably 5.0% by mass to 10.0% by mass, based in each case on the total mass of the recycled substream.

In a preferred embodiment, step (iv) is configured such that the quench liquid is injected into the reaction product mixture at just one position in the quench zone (one-stage quench). What is meant here by "at just one position" is a single position in the longitudinal direction of the reactor in a quench zone in an upright reactor having a round (especially circular symmetrical) cross section. It is quite possible here for the quench liquid to be distributed with the aid of multiple nozzles over the cross section of the quench zone. However, this is accomplished at the same position in the longitudinal direction of the reactor, by contrast with the procedure shown in FIG. 1 with supply of quench liquid at two different positions (see 116 and 105) in the longitudinal direction of the reactor.

The temperature of the quench liquid used in step (iv) is preferably chosen such that it is firstly high enough to cleave the carbamoyl chloride corresponding to the isocyanate to isocyanate and hydrogen chloride. (It is in no way certain whether the carbamoyl chloride intermediate known from the liquid phase phosgenation will also be formed in the gas phase phosgenation. Since, however, it is independently conceivable that liquefied isocyanate reacts partly with the hydrogen chloride gas present in the quench to give the carbamoyl chloride, the temperature of the quench liquid should be high enough to suppress this reaction.) On the other hand, isocyanate and any solvent additionally used as diluent in the gaseous amine stream and/or gaseous phosgene stream should very substantially condense or very substantially dissolve in the solvent, while excess phosgene, hydrogen chloride and any inert gas used additionally as diluent pass through the quench zone very substantially uncondensed and undissolved, such that the temperature of the quench liquid chosen must not become too high either. Of particularly good suitability for selectively obtaining the isocyanate from the gaseous reaction mixture are quench liquids kept especially at a temperature of 50° C. to 250° C., preferably 100° C. to 200° C., more preferably 120° C. to 190° C. (if multiple streams of quench liquid are used, the temperature of each stream of quench liquid is kept within this range). The mass flow rate of quench liquid used overall in step (iv) is preferably chosen here such that it is 2 times to 60 times, more preferably 10 times to 50 times, most preferably 20 times to 40 times, the mass flow rate of gaseous stream of the primary amine from step (i).

At a given temperature, pressure and composition, it is easy for the person skilled in the art on the basis of the physical data to predict what proportion by mass of the isocyanate will condense in the quench and what proportion will run through it uncondensed. It is likewise easy to predict what proportion by mass of the excess phosgene, hydrogen chloride, any solvent and any inert gas used as diluent will run through the quench uncondensed and what proportion will dissolve in the quench liquid. The mixture of reaction product mixture and quench liquid thus obtained in the quench zone therefore contains gaseous components and liquid components, i.e. is biphasic.

Mixing zone, reaction zone and quench zone are preferably disposed in a common apparatus, the reactor. Especially preferably, the reactor has a round (especially circular symmetrical) cross section in the region of the mixing zone, reaction zone and quench zone and is either cylindrical in shape or has—as described above—sections of different cross section, such that the reactor consists of cylinders of different diameter in the region of the mixing zone, reaction zone and quench zone, connected via conical transition pieces. The reactor here is preferably upright, and the amine and phosgene reactant gas streams (and the intermediates and end products formed therefrom) preferably pass through the reactor from the top downward. In that case, mixing zone, reaction zone and quench zone are arranged in that sequence from the top downward in the reactor. Preferably, the collecting zone outlined in detail hereinafter is also part of the reactor and, in the case of an upright arrangement thereof, is especially disposed below the quench zone. The collecting zone also preferably has a round (especially circular symmetrical) cross section; but other configurations are conceivable.

In step (v), the mixture of reaction product mixture and quench liquid obtained in step (iv) is guided into a collecting zone for phase separation.

In the above-detailed preferred embodiment of the common arrangement of mixing zone, reaction zone, quench zone and collecting zone from the top downward in that sequence in an upright reactor, the mixture of reaction product mixture and quench liquid obtained in step (iv) flows under gravity (i.e. "automatically") into the collecting zone. In another arrangement of the collecting zone, it may be necessary under some circumstances to pump the mixture of reaction product mixture and quench liquid into the collecting zone.

In the collecting zone, a separation of the mixture of reaction product mixture and quench liquid obtained in step (iv) into a liquid phase comprising isocyanate and optionally solvent and a gaseous phase comprising (at least) hydrogen chloride, unconverted phosgene and unliquefied isocyanate and any evaporated solvent takes place. The liquid phase and gaseous phase are withdrawn continuously from the collecting zone.

What is essential to the invention is that a liquid solvent stream comprising more than 50.0% by mass, especially at least 51.0% by mass, preferably at least 80.0% by mass, more preferably at least 90.0% by mass, most preferably at least 99.0% by mass, organic solvents, based on the total mass of the solvent stream, is additionally introduced into this collecting zone or into a collecting tank for liquid phase obtained in the collecting zone which is in flow direction downstream of the collecting zone. In this way, it is possible to adjust the viscosity of the liquid crude product in a controlled manner to a desired value suitable for further processing. It is also possible in this way to further lower the temperature of the mixture of reaction product mixture and quench liquid and in this way to minimize unwanted side reactions. Preferably, the organic solvent present in the abovementioned proportions in the liquid solvent stream is selected from the group consisting of aliphatic hydrocarbons [preferably decahydronaphthalene], aromatic hydrocarbons having no halogen substitution [preferably toluene or xylene, especially toluene], aromatic hydrocarbons having halogen substitution [preferably chlorobenzene, para-dichlorobenzene, ortho-dichlorobenzene, chlorotoluene or chloronaphthalene, especially ortho-dichlorobenzene] and mixtures of the aforementioned organic solvents. The temperature of the liquid solvent stream guided into the collecting zone or into a downstream collecting tank in this step (v) is preferably in the range from 120° C. to 200° C., more preferably in the range from 180° C. to 190° C. The flow rate of the liquid solvent stream guided into the collecting zone in the first variant of the invention is preferably chosen such that its proportion in the total mass of the liquid phase which forms in the collecting zone and in this case always contains solvent as well as isocyanate is in the range from 20% by mass to 80% by mass, more preferably in the range from 40% by mass to 60% by mass. If the liquid solvent stream in the second variant of the invention is guided solely into the collecting tank, the numerical values mentioned are correspondingly applicable to the liquid phase present in the collecting tank, meaning that the solvent stream content in this liquid phase based on the total mass of liquid phase in the collecting tank is preferably in the range from 20% by mass to 80% by mass, more preferably in the range from 40% by mass to 60% by mass. In the third variant of the invention, as is preferred in the second variant, a solvent stream content in the liquid phase based on the total mass of said liquid phase in the collecting tank in the range from 20% by mass to 80% by mass, more preferably in the range from 40% by mass to 60% by mass, is established. The third variant allows the solvent stream that preferably comes from step (viii) which is still to be outlined in detail further down (cf. also the abovementioned fifteenth embodiment) to be divided between the collecting zone and the collecting tank in accordance with the specific demands that exist in a particular situation. If the aim is, for example, to particularly rapidly further cool the mixture of reaction product mixture and quench liquid coming from step (iv), it is possible to increase the proportion of the solvent stream guided into the collecting zone at the expense of the proportion guided into the collecting tank. For this purpose, it is of course necessary for there to be appropriate conduits provided with control valves, as described in detail further down in the elucidation of FIG. 3.

What is meant by the "total mass of the liquid phase" in all variants outlined above and embodiments thereof is the mass of the respective liquid phase including the mass of liquid solvent stream supplied, irrespective of whether it is introduced into the collecting zone or into a downstream collecting tank.

In step (v), a liquid phase comprising (at least) isocyanate and solvent and a gaseous phase comprising (at least) hydrogen chloride, unreacted phosgene, unliquefied isocyanate and any evaporated solvent are thus obtained.

To obtain the isocyanate from the liquid phase comprising isocyanate and solvent which is obtained in step (v), this phase is preferably subjected to further workup to give pure isocyanate.

The workup can be conducted with the entire liquid stream obtained in step (v). However, it is likewise possible to send just a substream of this liquid phase to the workup and to cool the remainder in a step (vi) and recycle into the quench from step (iv). More particularly, therefore, the invention also relates to a process in which the quench liquid used in step (iv) comprises and especially consists of a portion of the liquid phase comprising isocyanate and optionally solvent which is obtained in step (v), which is cooled, preferably by indirect cooling (i.e. without direct (physical) contact of the liquid phase withdrawn from the collecting zone with a liquid cooling medium), but is otherwise unchanged in its composition. A heat exchanger is especially suitable for the purpose of indirect cooling in step (vi). The cooling in step (vi) is preferably effected to a temperature in the range from 30° C. to 245° C., preferably 80° C. to 195° C., more preferably 100° C. to 195° C., most preferably 100° C. to 185° C. Since this recycled liquid phase does not undergo any further treatment apart from the cooling, i.e. any further change, its composition in this embodiment corresponds to that of the liquid phase in the collecting zone.

Furthermore, the efficiency of the cooling of liquid phase withdrawn from the collecting zone by an external heat exchanger by the process of the invention can be increased considerably since the heat capacity of liquid phase is comparatively high owing to its reduced solvent content compared to the prior art (FIG. 1). Moreover, when the process of the invention is used, the efficiency of the external heat exchanger is additionally increased since the isocyanate now having only comparatively low solvent dilution, owing to the better dissolution properties for residue components, is able to effectively protect the surfaces of the heat exchanger from deposits.

In one embodiment of the invention, the liquid phase present in the collecting zone, even before it has been withdrawn, can be cooled by recycling of a condensate from the residue workup—described in detail hereinafter—that consists almost entirely or completely of the isocyanate to be prepared (especially to an extent of 95% by mass to 100% by mass, based on the total mass of the condensate). This recycling firstly enables additional cooling of the liquid phase obtained in the collecting zone with reduction of the amount of isocyanate evaporated (i.e. with reduction of the gas phase formed step (v) and withdrawn from the collecting zone); secondly, the residue concentration in the bottom of the reactor can be kept low by dilution. The cooling effect is accompanied by heating of the condensate from the residue workup, which leads to a saving of energy since this material would otherwise have to be heated up again in the isocyanate distillation stage.

In further embodiments, sufficiently cooled isocyanate streams from any process steps can be recycled into the collecting zone in order to lead to cooling and dilution therein.

Preferably 50% to 96%, more preferably 60% to 94%, most preferably 70% to 92%, of the liquid phase withdrawn from the collecting zone in step (v) is recycled into step (vi) as quench liquid, while the remainder is sent to a workup to obtain pure isocyanate. This is done either directly (meaning that the liquid phase withdrawn from the collecting zone is worked up without further intermediate steps) or after the feeding of a solvent stream into the collecting tank which is envisaged in the second and third variants. In each case, the process of the invention, in particularly preferred embodiments, enables the provision of a liquid crude product to be sent to the workup (i.e. the crude product after addition of the entire solvent stream from step (v)) having a content of organic solvents of 2.0% by mass to 20% by mass, preferably of 2.0% by mass to 8.0% by mass, more preferably of 2.0% by mass to 4.0% by mass, based on the total mass of liquid crude product to be sent to the workup.

The already mentioned workup of the liquid phase comprising isocyanate and solvent (from the addition to the collecting zone and/or to the collecting tank) from step (v) to give pure isocyanate, which is conducted with preference, is preferably effected by distillation (step vii). Especially preferably, first of all, in a first distillation step (vii-1), in what is called a solvent column, the majority of the solvent is removed, followed by, in at least one further distillation step (vii-2), a fine purification of isocyanate. The workup can be conducted as known from the prior art, especially as described in EP 1 371 633 A1. It is likewise possible for the distillation step (vii-1) to be preceded by a separate removal of dissolved phosgene and dissolved hydrogen chloride which is known from the prior art (step (vii-0)). The fine purification of isocyanate in step (viii-2) is preferably effected in a single distillation column which may especially be configured as a dividing wall column.

Irrespective of the exact configuration of the distillative workup in step (vii), at least one distillation bottom stream is also obtained as well as the pure isocyanate obtained (as distillate stream) (for example the distillate bottom stream from the dividing wall column used in step (vii-2) in a preferred embodiment of the invention). This distillation bottom stream contains what is called the distillation residue and proportions of isocyanate to be prepared.

The distillation residue contains compounds that do not evaporate under the pressure and temperature conditions chosen for the distillation or that do not evaporate without decomposition at all. The compounds in the distillation residue that are evaporable with difficulty, if at all—if they are not impurities from the primary amine used that run through the phosgenation process unchanged—are phosgenation products of high molecular weight, the structure of which is still not exactly known. For instance, they may be compounds that can be derived (in a formal sense) from polymerization products of the amine used by replacement of the unpolymerized amine groups by isocyanate groups. Phosgenation products of higher molecular weight may also partly form (by further reaction) in step (vii).

The distillation bottom stream containing the distillation residue is preferably likewise worked up (step vii-3)), wherein this workup comprises the following steps:
a) optionally preconcentrating the distillation bottom stream in an evaporator by partially evaporating the isocyanate to be prepared which is present in the distillation bottom stream to obtain a pre-concentrated liquid stream depleted of isocyanate to be prepared;
b) drying of the distillation bottom stream or the preconcentrated liquid stream depleted of isocyanate to be prepared which has been obtained in step a) in a drying apparatus at a temperature in the range from 150° C. to 500° C., preferably in the range from 185° C. to 300° C., more preferably in the range from 200° C. to 270° C., and at a pressure in the range from 10 $mbar_{(abs.)}$ to 250 $mbar_{(abs.)}$ preferably in the range from 20 $mbar_{(abs.)}$ to 200 $mbar_{(abs.)}$, more preferably in the range from 30 $mbar_{(abs.)}$ to 100 $mbar_{(abs.)}$ is conducted, with evaporation and recovery of isocyanate to be prepared to form a solid process product.

This optional preconcentration by partial evaporation in step a) can in principle be effected in any evaporators known to those skilled in the art. More preferably, step a) is conducted in an evaporator selected from the group consisting of thin-film evaporators, climbing-film evaporators, falling-film evaporators, long tube evaporators, helical tube evaporators, forced circulation flash evaporators and a combination of these apparatuses. Particular preference is given here to falling-film evaporators. It is also possible to connect multiple evaporators in series. The preconcentration in step a) is preferably effected at a temperature in the range from 120° C. to 180° C. and at a pressure in the range from 20 $mbar_{(abs.)}$ to 60 $mbar_{(abs.)}$, more preferably at a temperature in the range from 130° C. to 175° C. and at a pressure in the range from 25 $mbar_{(abs.)}$ to 45 $mbar_{(abs.)}$. Step a) can be conducted continuously or batchwise. The continuous process regime is preferred.

In step b), the preconcentrated liquid stream that has been depleted of isocyanate to be prepared and is obtained in step a) or—when step a) is dispensed with—the distillation bottom stream is dried. Drying apparatuses suitable for step b) are preferably selected from the group consisting of heated, product-agitating vacuum driers with a horizontal shaft (preferably kneader-driers, paddle driers, shovel driers; wherein each of the driers mentioned may have exactly one shaft or multiple shafts, especially two shafts), rotary tubes, disk driers, belt driers and pelletizing screws. In the drying, the isocyanate to be prepared is evaporated and recovered. What remains is a solid material consisting virtually exclusively of distillation residue and still containing the isocyanate to be prepared in traces at most. The solid is preferably discharged continuously from the drying apparatus.

The isocyanate evaporated in step a) or in steps a) and b) is condensed. In the case of performance of steps a) and b), the condensates obtained are preferably combined. The proportion of isocyanate to be prepared which is recovered in this way is preferably combined partly to completely, preferably completely, with the pure isocyanate or recycled elsewhere in the process. It is possible, for example, to recycle the proportion of the isocyanate to be prepared that is obtained in step (vii -3) into step (vii-2), especially into the feed or into the distillation bottom stream of the distillation column used therein (in the case of multiple distillation columns connected in series preferably into the feed or into the distillation bottom stream of the last distillation column). In another embodiment, the isocyanate condensate obtained, as already described further up, is used for direct (pre) cooling of the liquid phase containing in the collecting zone.

Preference is also given to working up the gaseous phase comprising hydrogen chloride, unconverted phosgene, unliquefied isocyanate and any evaporated solvent which is obtained in step (v) (step (viii)).

In this further workup, unliquefied isocyanate in particular is recovered, and solvents (if present in the gas phase withdrawn from the collecting zone in step (v)), excess phosgene and hydrogen chloride gas formed are separated from one another.

The isocyanate recovered is recycled into the process, as elucidated in detail hereinafter. For economic reasons, the solvent is preferably also fed back to the process. More particularly, it is preferable to use the recovered solvent as a constituent, optionally as the sole constituent, of the liquid solvent stream to use in step (v), as elucidated in detail further down. For economic reasons, phosgene is preferably likewise fed back to the reaction, especially to step (i). The hydrogen chloride recovered can be sent to various possible uses, for example an oxychlorination of ethylene to ethylene dichloride or a recycling process that affords chlorine, which can be recycled back into the isocyanate process. These recycling processes include the catalytic oxidation of hydrogen chloride, for example by the deacon process, the electrolysis of gaseous hydrogen chloride and the electrolysis of an aqueous solution of hydrogen chloride (hydrochloric acid), obtained by absorption of the hydrogen chloride formed in water.

In step (viii), initially unliquefied isocyanate is recovered from the gaseous phase withdrawn from the collecting zone in step (v).

The procedure for performance of step (viii) may be such that the gaseous phase obtained in step (v) comprising hydrogen chloride, unconverted phosgene, unliquefied isocyanate and any evaporated solvent is firstly condensed in a step (viii-1) by cooling (i.e. indirect cooling [i.e. without physical contact with a liquid heat transfer medium]; this cooling is preferably conducted in a heat exchanger) to obtain a liquid stream comprising optionally solvent and isocyanate and a gaseous stream comprising hydrogen chloride, phosgene, any unliquefied isocyanate and any unliquefied solvent, in a particular configuration of this embodiment only partly condensed (i.e. the liquefaction of solvent (if present) and isocyanate is deliberately incomplete).

In the case of sufficient condensation of the isocyanate in the condensation (viii-1), the gaseous phase obtained—since it has been largely to completely freed of isocyanate—can be sent directly to further workup for recovery of phosgene and hydrogen chloride. The condensed phase, depending on its composition, can be sent either to the workup in step (vii) or—preferably—used in step (v) as liquid solvent stream which is supplied to the collecting zone or a collecting tank arranged in flow direction downstream thereof (or as a portion thereof). The latter naturally assumes that the condensed phase contains sufficient solvent, which is regularly the case in the first and third variants of the invention (since a portion of the solvent introduced into the collecting zone is evaporated and liquefied again in the condenser from (viii-1) therein), and is the case in the second variant when the quench liquid from step (iv) comprises enough solvent.

In the case of only partial condensation in step (viii-1), it is preferable to guide the resultant gaseous stream comprising hydrogen chloride, phosgene, any unliquefied isocyanate and any unliquefied solvent into a scrubbing column for removal of residual isocyanate in a step (viii-2) and to contact it therein with at least one liquid solvent stream (i.e. a stream containing more than 50.0% by mass, especially at least 51.0% by mass, preferably at least 80.0% by mass, more preferably at least 90.0% by mass, most preferably at least 99.0% by mass, based on the total mass of the solvent stream, of organic solvents) as scrubbing liquid, giving a liquid stream comprising solvent and isocyanate and a gaseous stream comprising hydrogen chloride and phosgene.

Figure 2A:
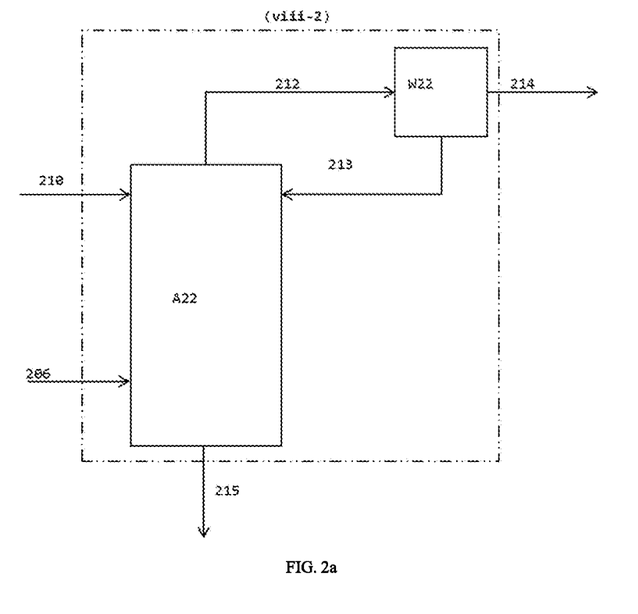
FIG. 2a is a detail enlargement of the scrubbing column of FIG. 2b and FIG. 2c.
Figure 2B:
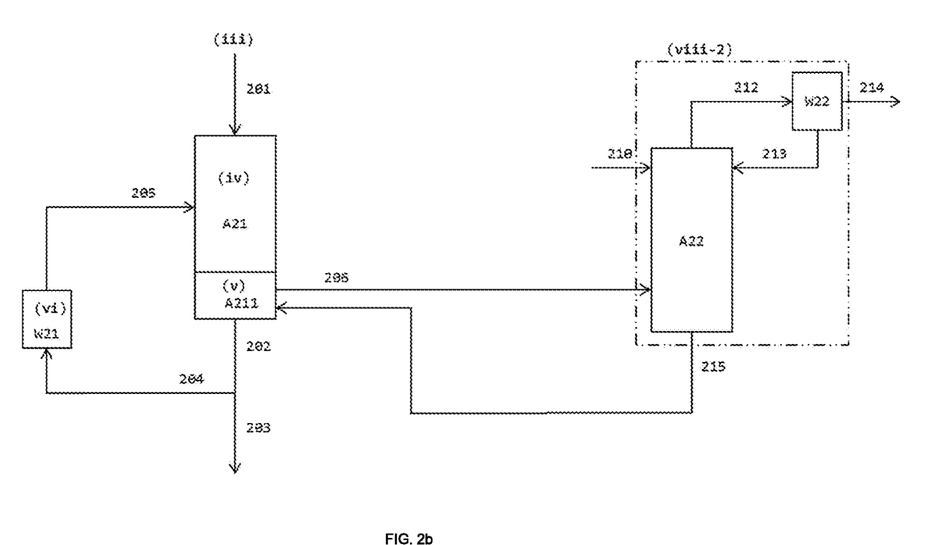
FIG. 2b illustrates a process flow whereby a liquid solvent stream guided into a collecting zone or a downstream collecting tank comprises a liquid stream comprising solvent and isocyanate and does not comprise any further streams.

Suitable scrubbing columns are known to the person skilled in the art. Examples include packed columns and tray columns. There follows a general elucidation of the operation of such a scrubbing column in step (viii-2) with reference to FIG. 2a (FIG. 2a is a detail enlargement of the scrubbing column from FIG. 2b and FIG. 2c; however, the description that follows is not limited to the embodiments according to FIG. 2b and FIG. 2c, but is applicable to all embodiments of the invention):

The gaseous material flow (206 in FIG. 2a) that is to be freed of isocyanate by scrubbing is fed to the scrubbing column (A22). The scrubbing liquid required for the purpose is applied at the top of the scrubbing column (A22). The vapors (212) from the scrubbing column pass through a condenser (vapor condenser W22). Of course, it is also possible to use two or more condensers of this kind, especially two, connected in series; it is generally the case that, when the description of the invention refers to "an" apparatus and/or just one apparatus is shown in the drawings, unless stated otherwise, this does not rule out embodiments in which two or more apparatuses are used for the particular purpose. Fractions (213) that are liquefied in the condenser (W22) are returned to the top of and hence recycled into the scrubbing column. The uncondensed fractions (214) containing predominantly hydrogen chloride gas and phosgene, as described further down, are preferably worked up for recovery of hydrogen chloride and phosgene. The greater the isocyanate content in the material flow (206) supplied, the greater the flow rate of scrubbing liquid supplied at the top of the scrubbing column has to be, and the more separation plates are required for reliable retention. The overall scrubbing liquid used in step (viii-2) is composed of the condensate (213) from the condenser (W22) and additionally supplied wash liquid (210). This additionally supplied wash liquid (210) is a solvent stream containing an organic solvent selected from the group consisting of aliphatic hydrocarbons [preferably decahydronaphthalene], aromatic hydrocarbons having no halogen substitution [preferably toluene or xylene, especially toluene], aromatic hydrocarbons having halogen substitution [preferably chlorobenzene, para-dichlorobenzene, ortho-dichlorobenzene, chlorotoluene or chloronaphthalene, especially ortho-dichlorobenzene] and mixtures of the aforementioned organic solvents.

It is possible to guide the gaseous phase comprising hydrogen chloride, unconverted phosgene, unliquefied isocyanate and any evaporated solvent which is obtained in step (v) directly, i.e. without passing through the condensation in step (viii-1), into a scrubbing column from step (viii -2) and to contact it therein with at least one liquid solvent stream as scrubbing liquid, giving a liquid stream comprising solvent and isocyanate and a gaseous stream comprising hydrogen chloride and phosgene. The scrubbing liquid chosen is preferably a liquid solvent stream containing a solvent selected from the group consisting of aliphatic hydrocarbons [preferably decahydronaphthalene], aromatic hydrocarbons having no halogen substitution [preferably toluene or xylene, especially toluene], aromatic hydrocarbons having halogen substitution [preferably chlorobenzene, para-dichlorobenzene, ortho-dichlorobenzene, chlorotoluene or chloronaphthalene, especially ortho-dichlorobenzene] and mixtures of the aforementioned organic solvents. Preference is given to using the same solvent present in the liquid solvent stream guided into the collecting zone from step (v) or the downstream collecting tank. If the quench liquid used in step (iv) likewise contains solvent, it is preferably likewise selected from the aforementioned group.

In the majority of embodiments of step (viii) outlined above, liquid solvent streams containing small amounts of isocyanate are obtained (in the condenser used in step (viii-1) and in the scrubbing column used in step (viii-2)) and are suitable for being guided as a liquid solvent stream into the collecting zone or a downstream collecting tank in step (v). More particularly, therefore, the invention also relates to a process in which the liquid solvent stream guided into the collecting zone or a downstream collecting tank in step (v) comprises the liquid stream comprising solvent and isocyanate which is obtained in step (viii-1) and/or the liquid stream comprising solvent and isocyanate which is obtained in step (viii-2), if conducted, and especially does not comprise any further streams. This is shown by way of example for the embodiment using the scrubbing column from step (viii-2) (without prior condensation in step (viii-1)) in FIG. 2b. By contrast with FIG. 1, all reference numerals begin with the number 2 and otherwise have the same meaning as therein. The solvent content of stream 215 is adjusted via the choice of composition and flow rate of the scrubbing liquid (210) supplied and via the choice of condensation power of the condenser W22, which is material to the composition and flow rate of the recycle stream of recycled vapor condensate (213). Suitable scrubbing liquid (210) used for the scrubbing column A22 from step (viii-2) is a solvent stream as defined above in the general description of the scrubbing column. It should of course be noted here that the conditions—i.e. especially the flow rates of gas phase to be washed from the collecting zone (step (v); 206), of additionally supplied scrubbing liquid (210) and of recycled vapor condensate (213)—must be chosen such that the demands of the invention with regard to the maximum solvent content of the quench liquid in step (iv)—stream 205 here—are complied with.

Figure 2C:
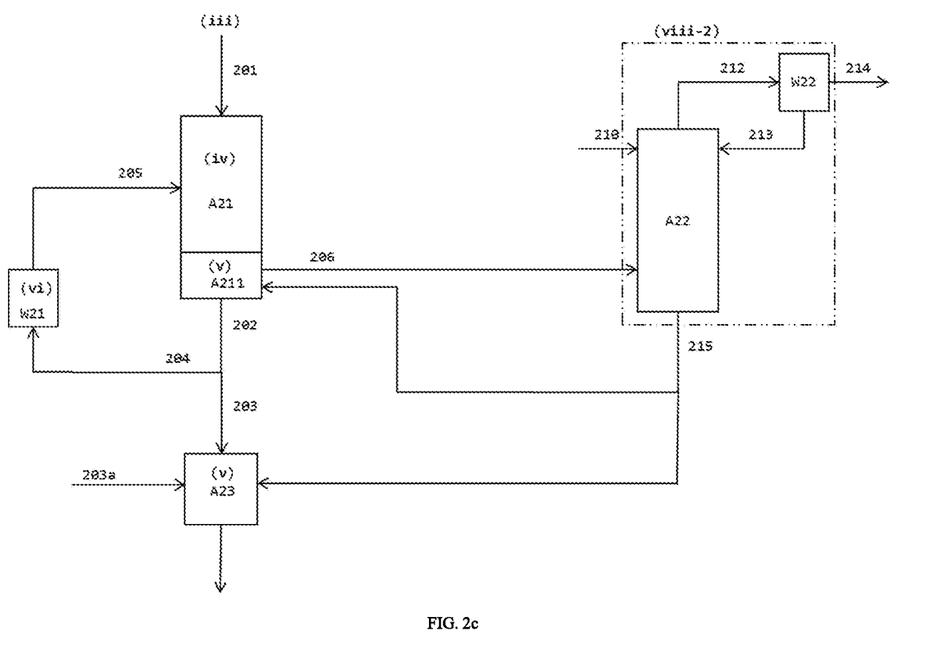
FIG. 2c illustrates an apparatus configuration of the invention.

FIG. 2c shows an apparatus configuration of the invention that can especially be used in the third variant (but also in the first and second variants):

The unrecycled fraction (203) of the liquid phase (202) from the collecting zone (A211) is guided into the collecting tank (A23). This collecting tank (A23) may additionally be fed with appropriate liquid streams (203a) from the collecting zones of other reaction lines. The liquid solvent stream (215) from the scrubbing column (A22) can be guided into the collecting tank (A211) and into the collecting zone (A23). The respective conduits have been provided here with control valves (not shown in the figure) that enable infinite regulation of the proportion of the solvent stream (215) guided into the collecting zone (A211) and the collecting tank (A23). It is also possible here for one of the two streams to be stopped completely, in accordance with the first variant of the invention when the solvent stream (215) into the collecting tank (A23) is stopped, or in accordance with the second variant of the invention when the solvent stream (215) into the collecting tank (A211) is stopped. It is possible by this apparatus construction to switch between the three variants of the invention within one production cycle, which increases the flexibility of the process.

Every reaction line may have its own scrubbing column (A22), in which case the streams (215a) obtained therein are likewise guided into the collecting tank (A23) common to all reaction lines. However, it is likewise possible for different reaction lines to have a common scrubbing column (A22), in which case the gaseous phases (206a) obtained in the respective collecting zones are likewise guided into the common scrubbing column (A22). These two alternatives are shown by dotted arrows in the figure.

The gaseous stream (214 in FIGS. 2a-c) obtained in step (viii-1) or step (viii-2) is preferably freed of excess phosgene in a step (viii-3) in a manner known per se. This can be effected by means of a cold trap, adsorption in an inert solvent (preferably selected from the group consisting of aliphatic hydrocarbons [preferably decahydronaphthalene], aromatic hydrocarbons having no halogen substitution [preferably toluene or xylene, especially toluene], aromatic hydrocarbons having halogen substitution [preferably chlorobenzene, para-dichlorobenzene, ortho-dichlorobenzene, chlorotoluene or chloronaphthalene, especially ortho-dichlorobenzene] and mixtures of the aforementioned organic solvents) or by adsorption and hydrolysis on activated carbon. This step is preferably effected as described in WO2011/003532 A1; see especially page 11 line 31 to page 25 line 15. The gas stream consisting essentially of hydrogen chloride which is obtained in the phosgene removal can be processed further in the manner outlined above.

In all steps of the process of the invention in which an organic solvent is used, preference is given to using the same organic solvent which is especially selected from the group consisting of aliphatic hydrocarbons [preferably decahydronaphthalene], aromatic hydrocarbons having no halogen substitution [preferably toluene or xylene, especially toluene], aromatic hydrocarbons having halogen substitution [preferably chlorobenzene, para-dichlorobenzene, ortho-dichlorobenzene, chlorotoluene or chloronaphthalene, especially ortho-dichlorobenzene] and mixtures of the aforementioned organic solvents. Particular preference is given to the use of ortho-dichlorobenzene.

The process of the invention has a series of advantages, especially:
a) reduction of internal solvent circulations;
b) decrease in size of solvent distillation in step (vii-1)
c) corresponding saving of evaporation energy to be introduced;
d) reduction in the vapor volumes leaving the collecting zone and hence reduction in size of downstream apparatuses (for example of the isocyanate scrubbing column);
e) higher efficiency of the reactor bottom cooler through maximized heat transfer.

The invention claimed is:

1. A process for preparing an isocyanate by phosgenating a corresponding primary amine in the gas phase, comprising:
   (i) providing a gaseous stream of a primary amine;
   (ii) providing a gaseous phosgene stream;
   (iii) mixing the gaseous stream of the primary amine from step (i) and the gaseous phosgene stream from step (ii) to give a gaseous reaction mixture while maintaining a stoichiometric excess of phosgene relative to primary amino groups in a mixing zone and conducting the gaseous reaction mixture thus obtained through a reaction zone for reaction of the primary amine with phosgene to obtain a gaseous reaction product mixture;
   (iv) cooling the gaseous reaction product mixture obtained after passage through the reaction zone from step (iii) by contacting the gaseous reaction product mixture with at least one stream of a quench liquid in a quench zone, where the total quench liquid used, based on its total mass, comprises organic solvents in a proportion of at most 50.0% by mass, where the remainder to 100% by mass comprises the isocyanate to be prepared, to obtain a mixture of reaction product mixture and quench liquid;
   (v) conducting the mixture of reaction product mixture and quench liquid obtained in step (iv) into a collecting zone for separation of a liquid phase and a gaseous phase to obtain a liquid phase comprising isocyanate and optionally organic solvent and a gaseous phase comprising hydrogen chloride, unconverted phosgene, unliquefied isocyanate and any evaporated organic solvent, wherein a liquid solvent stream comprising more than 50.0% by mass of organic solvents, based on the total mass of the liquid solvent stream, is introduced into the collecting zone, into a collecting tank for the liquid phase obtained in the collecting zone which is disposed in flow direction downstream of the collecting zone, or into both the collecting zone and the collecting tank.

2. The process as claimed in claim 1, in which the liquid solvent stream in step (v) is guided solely into the collecting zone, where the liquid solvent stream is guided at a flow rate such that the liquid solvent stream is present in an amount of 20% by mass to 80% by mass, based on the total mass of liquid phase that forms in the collecting zone.

3. The process as claimed in claim 1, in which the liquid solvent stream in step (v) is guided (a) into the collecting tank or (b) into the collecting tank and into the collecting zone, where the liquid solvent stream is guided at a flow rate such that the liquid solvent stream is present in an amount of 20% by mass to 80% by mass, based on the total mass of liquid phase that forms in the collecting tank.

4. The process as claimed in claim 1, in which the gaseous phase comprising hydrogen chloride, unconverted phosgene, unliquefied isocyanate and any evaporated solvent which is obtained in step (v) is at least partly condensed in step (viii-1) by indirect cooling to obtain a liquid stream comprising isocyanate and optionally solvent and a gaseous stream comprising hydrogen chloride, phosgene, any unliquefied isocyanate and any unliquefied solvent.

5. The process as claimed in claim 4, in which the gaseous stream comprising hydrogen chloride, phosgene, any unliquefied isocyanate and any unliquefied solvent which is obtained in step (viii-1) is guided, in a step (viii-2), into a scrubbing column, where it is contacted with a scrubbing liquid comprising at least one liquid organic solvent stream having an organic solvent content of more than 50.0% by mass, thereby giving a liquid stream comprising organic solvent and isocyanate and a gaseous stream comprising hydrogen chloride and phosgene.

6. The process as claimed in claim 1, in which the gaseous phase comprising hydrogen chloride, unconverted phosgene, unliquefied isocyanate and any evaporated solvent which is obtained in step (v) is guided, in a step (viii-2), into a scrubbing column, where it is contacted with a scrubbing liquid comprising at least one liquid organic solvent stream having an organic solvent content of more than 50.0% by mass, giving a liquid stream comprising solvent and isocyanate and a gaseous stream comprising hydrogen chloride and phosgene.

7. The process as claimed in claim 4, in which the gaseous phase comprising hydrogen chloride, unconverted phosgene and unliquefied isocyanate which is obtained in the collecting zone comprises evaporated solvent and the liquid solvent stream guided into the collecting zone or collecting tank in step (v) comprises the liquid stream comprising isocyanate and solvent which is obtained in step (viii-1).

8. The process as claimed in claim 5, in which the liquid solvent stream guided into the collecting zone or collecting tank in step (v) comprises the liquid stream comprising solvent and isocyanate which is obtained in step (viii-2).

9. The process as claimed in claim 7, in which the solvent stream from step (v) does not comprise any further constituents apart from the liquid stream comprising isocyanate and solvent from step (viii-1).

10. The process as claimed in claim 1, in which, in step (v), the liquid solvent stream is guided at least temporarily into the collecting zone and into the collecting tank, where the conduits for the solvent stream that lead into the collecting zone and the collecting tank are controllable independently of one another.

11. The process as claimed in claim 1, in which a portion of the liquid phase obtained in step (v) is cooled down in a step (vi) and is recycled into the quench zone from step (iv).

12. The process as claimed in claim 1, in which at least a portion of the liquid phase obtained in step (v) is worked up in a step (vii) to give pure isocyanate.

13. The process as claimed in claim 1, in which the organic solvent present in the liquid solvent stream guided into the collecting zone or collecting tank in step (v) is selected from the group consisting of aliphatic hydrocarbons, aromatic hydrocarbons having no halogen substitution, aromatic hydrocarbons having halogen substitution and mixtures of the aforementioned solvents, and in which any organic solvent used in any other step of the process is the same in each case as the organic solvent contained in the liquid solvent stream guided into the collecting zone or collecting tank in step (v).

14. The process as claimed in claim 1, in which the primary amine is selected from the group consisting of tolylenediamine, diphenylmethanediamine, xylylenediamine, pentane-1,5-diamine, hexamethylene-1,6-diamine, isophoronediamine, diaminodicyclohexylmethane and mixtures of the aforementioned compounds.

15. The process as claimed in claim 1, in which the same organic solvent is used in all steps of the process in which an organic solvent is used, and the organic solvent is selected from the group consisting of aliphatic hydrocarbons, aromatic hydrocarbons having no halogen substitution, aromatic hydrocarbons having halogen substitution and mixtures of the aforementioned organic solvents.

16. The process as claimed in claim 5, in which the gaseous phase comprising hydrogen chloride, unconverted phosgene and unliquefied isocyanate which is obtained in the collecting zone comprises evaporated solvent and the liquid solvent stream guided into the collecting zone or collecting tank in step (v) comprises the liquid stream comprising isocyanate and solvent which is obtained in step (viii-1).

17. The process as claimed in claim 8, in which the solvent stream from step (v) does not comprise any further constituents apart from the liquid streams comprising isocyanate and solvent from step (viii-2).

18. The process as claimed in claim 6, in which the liquid solvent stream guided into the collecting zone or collecting tank in step (v) comprises the liquid stream comprising solvent and isocyanate obtained in step (viii-2).

19. The process as claimed in claim 16, in which the liquid solvent stream guided into the collecting zone or collecting tank in step (v) comprises the liquid stream comprising solvent and isocyanate obtained in step (viii-2).

20. The process as claimed in claim 16, in which the solvent stream from step (v) does not comprise any further constituents apart from the liquid stream comprising isocyanate and solvent from step (viii-1).

21. The process as claimed in claim 18, in which the solvent stream from step (v) does not comprise any further constituents apart from the liquid stream comprising isocyanate and solvent from step (viii-2).

22. The process as claimed in claim 19, in which the solvent stream from step (v) does not comprise any further constituents apart from the liquid streams comprising isocyanate and solvent from steps (viii-1) and (viii-2).

* * * * *